United States Patent [19]

Bible et al.

[11] Patent Number: 4,538,909

[45] Date of Patent: Sep. 3, 1985

[54] CIRCUIT BOARD INSPECTION APPARATUS AND METHOD

[75] Inventors: Robert E. Bible; Robert E. Bible, Jr., both of Rancho Santa Fe; Richard S. Mason, Escondido, all of Calif.

[73] Assignee: Automation Engineering, Inc., San Diego, Calif.

[21] Appl. No.: 497,656

[22] Filed: May 24, 1983

[51] Int. Cl.³ .............................................. G01N 21/32
[52] U.S. Cl. .................................... 356/237; 356/239
[58] Field of Search .............................. 356/237, 239; 250/492.2, 572, 562; 350/235, 236, 525, 448, 268; 358/106

[56] References Cited

U.S. PATENT DOCUMENTS

| | | | |
|---|---|---|---|
| 3,713,741 | 1/1973 | Sheehan, III | 356/165 |
| 3,814,520 | 6/1974 | Baker et al. | 356/71 |
| 3,857,637 | 12/1974 | Obenreder | 356/120 |
| 3,976,382 | 8/1976 | Westby | 356/120 |
| 3,976,383 | 8/1976 | Olsen | 356/166 |
| 4,185,298 | 1/1980 | Billet et al. | 358/106 |
| 4,236,181 | 11/1980 | Shibata et al. | 358/106 |
| 4,240,750 | 12/1980 | Kurtz et al. | 356/394 |
| 4,269,515 | 5/1981 | Altman | 356/394 |
| 4,277,175 | 7/1981 | Karasaki et al. | 356/378 |
| 4,277,802 | 7/1981 | Yoshida | 358/106 |

*Primary Examiner*—John E. Kittle
*Assistant Examiner*—Thomas C. Saitta
*Attorney, Agent, or Firm*—Brown, Martin & Haller

[57] ABSTRACT

Apparatus and method for illuminating circuit boards to quickly and efficiently inspect them for various imperfections. An intense light beam is directed at an oblique angle at the surface of the board to be inspected. Some of the light enters the board and is partially scattered while some of it is reflected from the opposite surface. A detector array positioned above the inspected surface is scanned over that surface and distinguishes light and dark areas. Any light opaque area such as a conductive path or pad is a dark area while portions of the board free of circuitry is interpreted as a light area by the detector. Signals from the detector may be employed for many purposes relating to the circuit pattern on the board.

25 Claims, 9 Drawing Figures

CIRCUIT BOARD INSPECTION APPARATUS AND METHOD

FIELD OF THE INVENTION

This invention relates generally to printed circuit board inspection and more particularly concerns a novel illumination means and method to facilitate such inspection.

BACKGROUND OF THE INVENTION

Circuit boards are generally insulative flat sheets, rigid or flexible, having a pattern of electrically conductive paths to which wires and electronic components may be connected. Terms such as printed circuit board and printed wiring board are frequently used for these devices. The pattern of conductors on the board surface typically consists of a multiplicity of generally straight line segments of variable width and direction, with pads of greater diameter at some intermediate position in the path or terminating a path. There may be holes through the centers of these pads and through the board through which wires or leads of electronic components are passed for connection to the pads.

Although techniques for manufacturing circuit boards are highly advanced, a number of possible defects prevent the manufacturing yield from being less than 100%. Thus it is desirable, and for some purposes imperative, to inspect each board for defects which could lead to inoperativeness of the electronic component or circuit of which the board is a part. Typical defects in the conductive pattern relate to line widths, line spacings, cracks or voids, rough edges, shorts or merging between conductive paths or pads, and hole irregularities. Such inspection may be done visually with microscopes and machines have been developed for automatic inspection of circuit boards. Wiring board inspection machines frequently use one or more electro-optical cameras with extraordinarily high resolution. High density boards have line widths and spacings as low as 0.003 inch. For such boards the resolution of the optical detector in the camera must be in the order of 0.001 to 0.0003 inch to adequately inspect the board.

Optical detectors typically employ semiconductor linear arrays of up to 2,048 detectors or photo diodes in a camera, each individual detector in the array measuring the light intensity to which it is exposed. A typical detector is 0.001 inch square. With the optics of a typical camera magnified by a ratio of 3:1, an instantaneous field of view at the wiring board of approximately 0.0003 by 0.3 inch can be obtained.

The camera and the wiring board are physically moved with respect to each other in order to scan the instantaneous field of view of the camera over the entire circuit board. A circuit board inspection machine of the type mentioned above is disclosed in U.S. Pat. No. 4,185,298.

Several different methods for illumination of the circuit board surface to be inspected have been devised. One process involves illuminating the inspected surface of the board from the side on which the detector is located. Another technique employs back lighting wherein the illumination passes through the board from the side opposite the detector.

In the front lighting technique the camera measures the light reflected from the wiring board surface. The differences between conductor reflectivity and nonconductor reflectivity is a crucial parameter. Differences in design and in the condition of the circuit board can result in non-detection of defects as well as false alarms where no defect exists. An example of the condition variations include the fact that conductive paths may be claen and bright or variably tarnished and dull. Further, a number of different materials may comprise the exposed surface of the conductive path. Also the surface contours of the conductive paths are variable, specifically where wiring boards are tinned the top surface may be convex thereby producing specular reflections of substantial variability. Thus reflective systems are not effective to determine circuit path width, nor do thay readily detect underetch, which is a rough bridge of conductive material between paths. Also a thin flexible board can, in effect, fool the reflective type system because a circuit path on the non-inspected side could be reflected through and spuriously indicate the presence of circuitry that does not exist on the surface of interest.

In systems using back lighting, the detectors in the camera measure light transmitted completely through the wiring board. All conductors are opaque and appear dark regardless of their surface condition so some of the problems associated with front lighting are avoided. A significant limitation associated with the back lighting technique is that it is generally usable only with boards having circuitry on one side. If the board has conductive paths on both sides, back lighting will cause dark areas or shadows to be detected by the camera whether they are on the inspected side or the back side of the board. Thus the information received by the camera would be an intermingling of the conductive paths on both sides and would prevent such inspection apparatus from producing useful results. Additionally, many boards have substantially an entire surface plated with a conductor which would be fully opaque to back lighting and therefore this kind of system would not be appropriate for a board of this type.

The problem common to most prior circuit board inspection systems is accurate and reliable discrimination between the conductive areas and the substrate.

SUMMARY OF THE INVENTION

Broadly speaking, this invention relates to method and apparatus for illuminating circuit boards to facilitate quality control inspection and more particularly comprises a means for illuminating the surface of a circuit board having conductive paths thereon with the result being, in effect, to illuminate the board surface from within the board itself.

The illumination system of this invention includes one or more light sources directed at an oblique angle to the circuit board surface to be inspected. A photodetector device positioned on the same side of the board and sensing a defined portion or field of view of the board just outside of the surface area illuminated provides signals indicative of light transmission or obstruction from directly beneath the portion of the board inspected by the detector. The detector may be a single line array of photo diodes or it may be formed in several other configurations to facilitate rapid circuit board inspection.

An alternative embodiment includes a threshold light source positioned underneath the circuit board on the opposite side from the main illumination sources and the detector. Another alternative embodiment for positively determining that there is a hole through the board at the position of a pad which should have a hole, comprises a second source of radiation, preferably a laser, a second detector and an output comparator.

By means of this invention, the disadvantages of top lighted reflective systems and back lighted systems as discussed above are overcome.

BRIEF DESCRIPTION OF THE DRAWING

The objects, advantages and features of this invention will be more readily appreciated from the following detailed description when read in conjunction with the accompanying drawing, in which.

DESCRIPTION OF THE PREFERRED EMBODIMENTS

Figure 1:
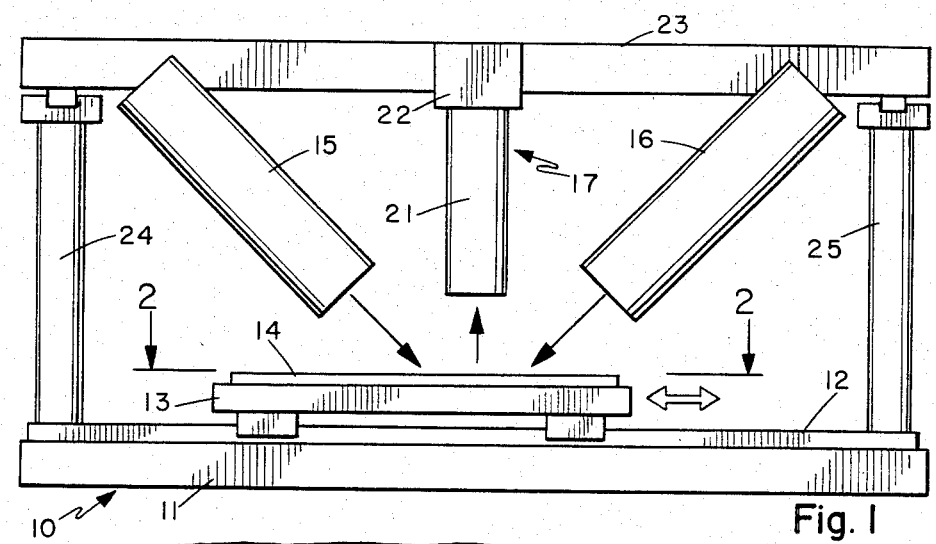
FIG. 1 is a mechanical schematic representation of structure for mounting the illumination system with respect to a curcuit board to be inspected.

With reference now to the drawing and more particularly to FIG. 1 thereof, a solid base 11 such as a block of granite provides a stable reference for the circuit board inspection machine 10. Mounted to the base are rails 12 and an open frame carriage 13 mounted for reciprocal motion on rails 12. Appropriate means are available for controlling movement of the carriage but such means are not shown and are not pertinent to the present invention. Circuit board 14 is mounted to the carriage, normally attached only at the edges, with the central portion of the circuit board being visible from beneath the carriage.

An optical system comprises two light sources 15 and 16 directed at oblique angles with respect to circuit board 14 and positioned on either side of a detector system 17. Appropriate optics are contained within cylinder 21 and a detector array is contained within camera body 22. The light sources and detector are mounted to frame element or carriage 23 which in turn is mounted to uprights 24 and 25 for reciprocal motion orthogonally with respect to the motion of carriage 13. The term "light" is employed herein generically and is not limited to visible radiation. It need only behave within this system in the manner described and it is only necessary that it be detectable by the sensor coupled to a computer, or visible on a scope or cathode ray tube.

In the course of operation, after the circuit board is mounted to the carriage, the optics are positioned at an appropriate starting point, such as over one corner of the board and either the optics or the board are moved with respect to the other so that the optical system scans one segment or strip of the board. The two main elements are then moved a relatively short distance in a stepping motion and the scan is accomplished once again. This is repeated until the entire board or desired portions have been scanned by the optical system.

Figure 9:
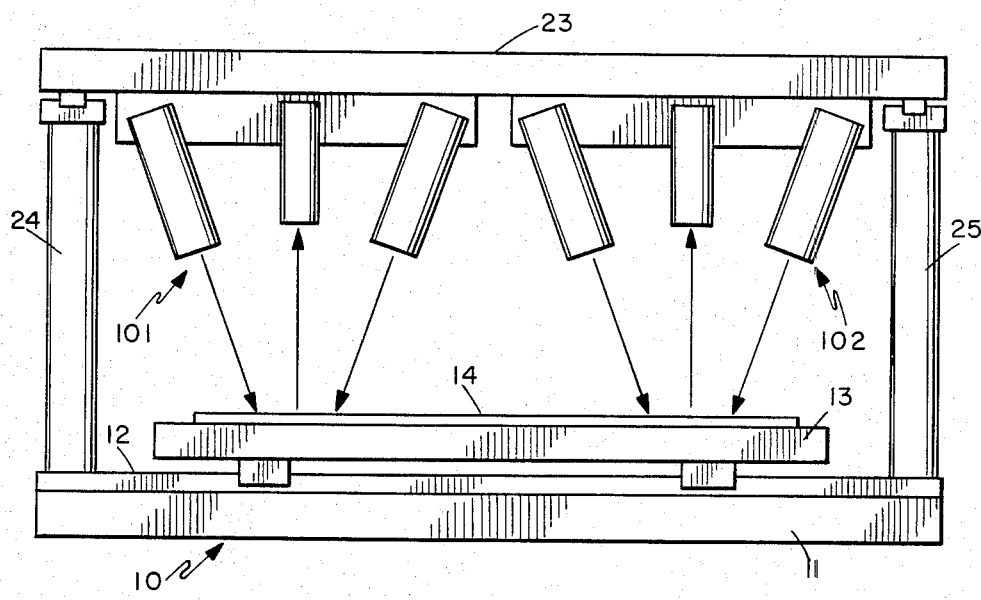
FIG. 9 is a mechanical schematic representation similar to FIG. 1 showing an additional embodiment.

The system shown in FIG. 1 is shown in duplicate form in FIG. 9. It should be observed that as many illumination units 101, 102 as desired may be mounted on carriage 23 to simultaneously illuminate and inspect more than one area of a circuit board or to inspect several circuit boards. Of course, each unit would have independent outputs. An illumination unit comprises the light sources, detector and approprate optics as necessary to control the area of the board surface being illuminated.

Figure 2:
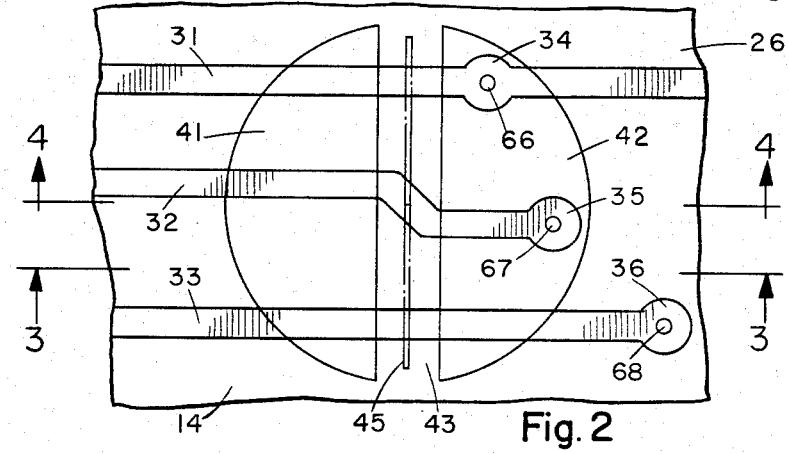
FIG. 2 is an enlarged plan view of a small portion of the surface of the circuit board being illuminated and indicating the relative position of the detector.
Figure 3:
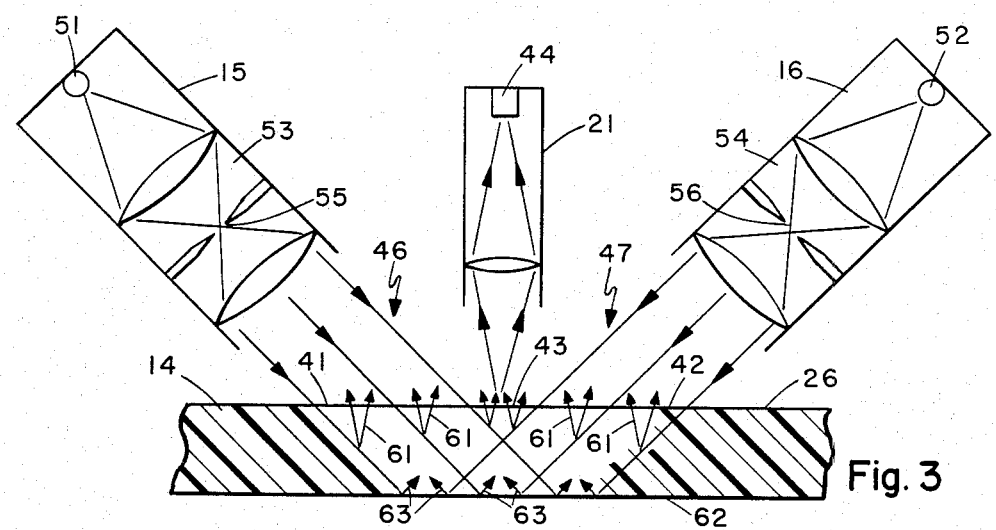
FIG. 3 is a diagrammatic sectional view of the optical system and circuit board taken along line 3—3 of FIG. 2.

With reference now to FIGS. 2 and 3, the top surface 26 of circuit board 14 is shown greatly enlarged in FIG. 2. Conductive paths 31, 32 and 33 having respective pads 34, 35 and 36 are partially illuminated as indicated by semicircles 41 and 42 spaced by gap 43 in the middle of which is positioned field of view 45 of the detector array 44. By way of example, the detector may be a linear array of as many as 2,048 photo diodes, such a detector array presently available from E G & G/Reticon. The field of view is typically 0.0003 inches wide, in gap 43 ranging between 0.005 and 0.03 inches wide. Light sources 15 and 16 provide oblique light beams 46 and 47 respectively for illumination of portions 41 and 42 of surface 26 of the circuit board. The light sources are conventional devices comprising appropriate lamps 51 and 52 with optics 53 and 54 and beam limiting apertures 55 and 56. The lamps are typically xenon arc bulbs. In order to keep gap 43 small, directly illuminated areas 41 and 42 must have sharp edges adjacent field of view 45. This is provided, for example, by apertures 55 and 56.

The circuit boards to be inspected by this system are translucent, typically having a glass fiber or fabric base, impregnated with epoxy, polyimide or polytetrafluoroethylene resin. Such circuit boards permit a certain amount of the light impinging on portions 41 and 42 of surface 26 to penetrate the board and to be scattered inside the board as indicated by arrows 61. Much of the light which reaches back side 62 of the board will be reflected as indicated by arrows 63 back toward and through front side 26. Because of the relative positions and angles of the light sources, a portion of the light is scattered and reflected into the otherwise dark area 43 of the board surface between lighted areas 41 and 42, some of it illuminating the field of view 45 of optical detector 44. The appropriate detector within the array of detectors 44 senses a relatively high level of illumination coming from within the board, indicating the absence of a conductor on the surface of the board. This would provide a relatively high output level by the detector.

Figure 4:
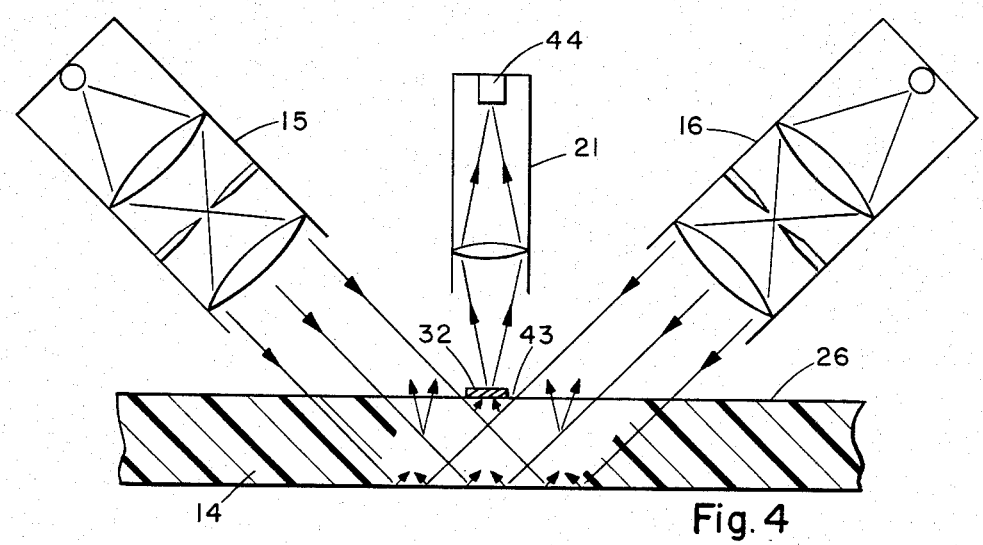
FIG. 4 is a diagrammatic sectional view of the optical system and circuit board taken along line 4—4 of FIG. 2.

FIG. 4 is similar to FIG. 3 except that a portion of conductive path 32 is in the field of view 45 of the optical detector. This conductive path blocks the light which is scattered and reflected within the circuit board into the non-illuminated gap 43 so that the appropriate sensor or sensors of detector 44 sees very little light and has a relatively very low output indicating the presence of a conductor.

When the embodiment shown in FIGS. 2-4 is employed, two orthogonally related passes of the illumination system with respect to the surface of the circuit board will provide complete information as to circuit path and pad size, continuity, proper spacing, rough edges, shorts, cracks and voids, hole sizes as well as conductive element locations.

This system, by looking at the top surface of the board, that is the surface to be inspected, can provide the desired information for substantially any translucent circuit board with different conductor conditions including positive or negative artwork, bright copper, tarnished copper, oxide-treated copper, tin lead plated circuitry, gold plated or silver plated circuitry or reflow solder coated conductors. It will handle backplaned lamina as well as double sided or multi-layer boards. The basic requirement is that, with respect to the wavelength of the illuminating radiation, the conductive portions must be opaque as compared with the circuit board substrate in the absence of conductive circuitry. Reflectivity or color of the conductive circuitry is irrelevant.

Figure 5:
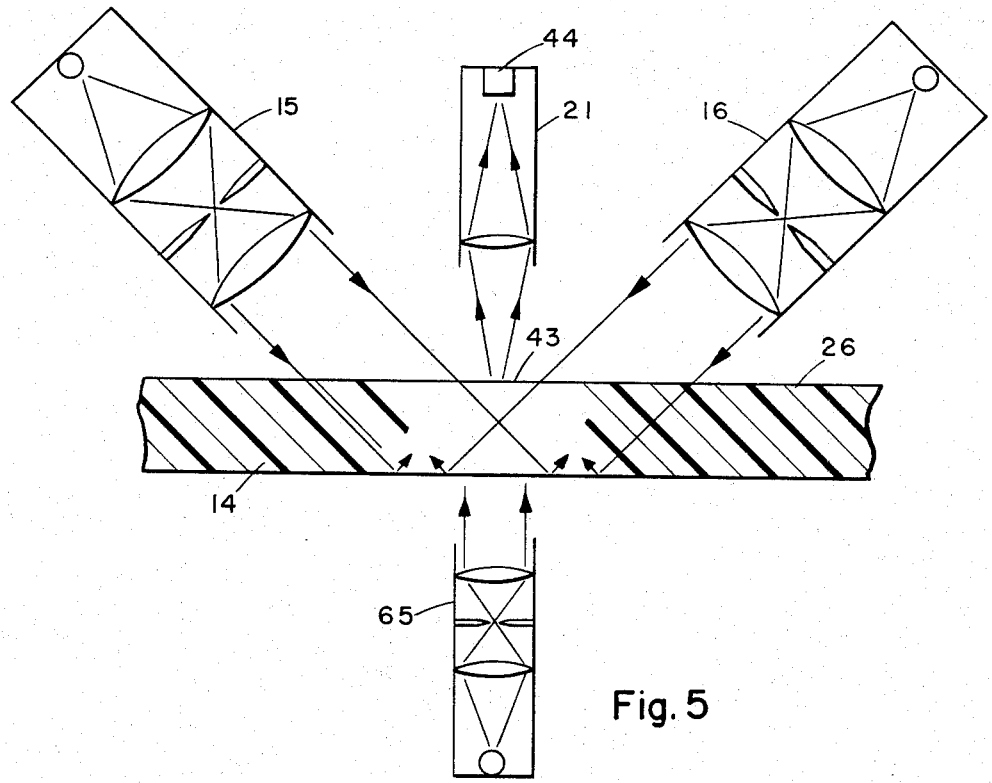
FIG. 5 is a diagrammatic sectional view similar to FIG. 4 showing an alternative embodiment with a reference back light.

An alternative embodiment is shown in FIG. 5 wherein a back or reverse light source 65 provides light from the back or underside of circuit board 14, typically focussed on the first lens of detector 17. This structure enhances the ability of the illumination system to determine the presence of holes such as plated through holes. The embodiment without the back light 65 of FIG. 5 can accurately determine conductive path widths, integrity, continuity and spacing but there is a limitation in the determination of holes 66, 67, 68 in pads 34, 35, 36 respectively (FIG. 2). If a hole, whether or not plated, exists through the board, there is no material through which the light may be propagated back up to be detected by camera 22. Thus it could not normally be detected by the illumination system of FIGS. 3 and 4. Additionally, if the substrate is thin, for example, 0.003 inch, rear side plating causes bright reflection on the front side in the field of view. Areas not plated on the back side result in a much lower level of detectable light. This could be accommodated by electronics or software in the inspection system, but is simply handled by providing a threshold light source on the back side to balance the light level being sensed. By providing a light source from beneath the board on the opposite side of detector 44, a consistent level of light is provided to the detector whenever an opaque conductive element is not directly beneath a detector element. This provides an improved signal-to-noise ratio and a reduced likelihood of false readings. By the configuration of FIG. 5, it is easily determined that an opening exists within the confines of a pad and it will determine location of the opening to determine whether it is appropriately centered.

Figure 7:
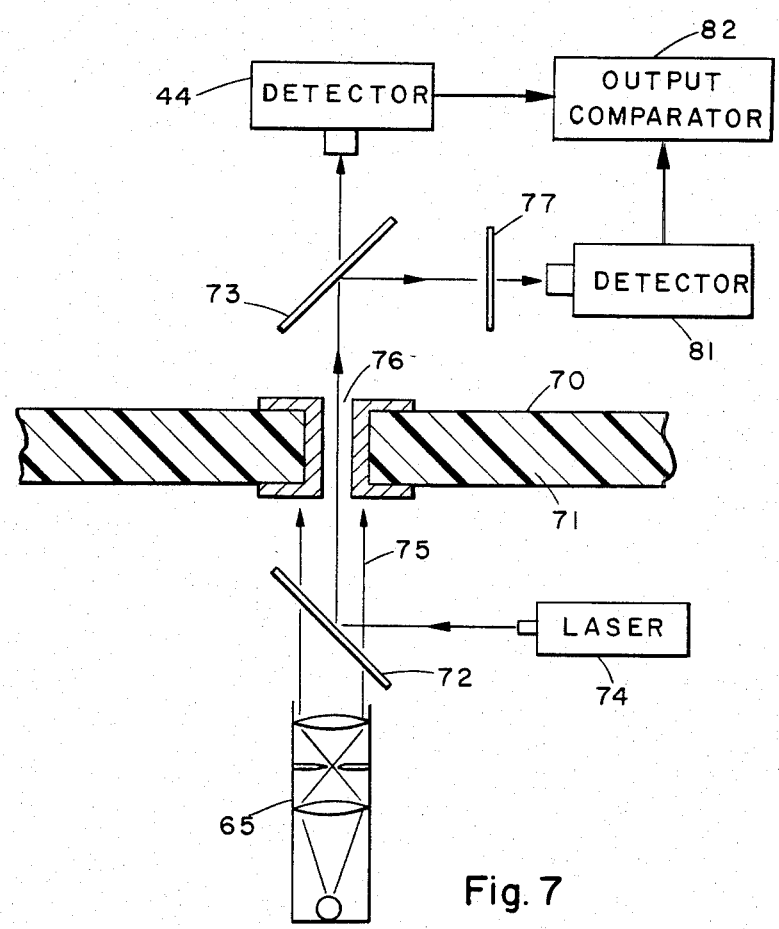
FIG. 7 is a schematic alternative embodiment with a laser detector for plated through holes.

A further alternative embodiment to determine whether or not a hole has actually been drilled through the board at a location where a hole is desired, is shown in FIG. 7. This uses the arrangement of FIG. 5 (the main light sources 15 and 16 are not shown so as not to complicate the figure) together with a laser and beam splitter apparatus coupled with a second detector and an output comparator. The light from source 65 is directed to the underside of board 71 in the same manner as shown in FIG. 5. Interposed between the light source and the board is beam splitter 72 which allows a significant portion of the back light to pass through it. Above the board and between the top surface 70 of board 71 and detector 44 is a second beam splitter 73 functioning in a similar manner to beam splitter 72. Laser 74 directs its light beam against beam splitter 72 centrally of collimated beam 75 of light source 65 so that it passes through hole 76 drilled through board 71, whether or not it is a plated through hole. The laser is then redirected by beam splitter 73, passes through filter 77 to detector 81. The beam splitters and filter are arranged so that substantially all of the laser beam is reflected by beam splitters 72 and 73 and only the laser frequency is passed by filter 77 to detector 81. Detector 44 operates in the same manner as in FIG. 5 but its output is transmitted to comparator 82 along with the output of detector 81. The frequency of the laser radiation is such that it will pass to detector 81 only when there is a hole through board 71. thus if the illumination system "sees" a pad and a hole pursuant to the setup with back light 65, if the laser radiation is not sensed by detector 81, it would indicate that while there are pads with openings in the conductive surface, the hole has not been drilled properly through the board.

Figure 6:
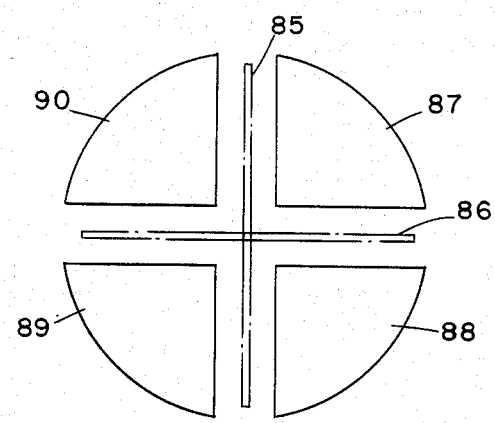
FIG. 6 is a plan view similar to FIG. 2 showing an alternative embodiment of the light beams and detector element.

Although the above discussion centers around the structure of FIG. 2 showing a line array of detectors, there is no practical or conceptual difficulty in arranging the detectors in a variety of configurations. One such configuration is shown in FIG. 6 where two linear detector arrays having cross-shaped fields of view 85, 86 are arranged in a crossed pattern so that only one pass of the illuminating system with respect to the circuit board would be necessary. The illuminated areas 87, 88, 89, 90 are pie shaped and have sharply defined edges spaced from but adjacent the fields of view. Similarly, the detector array could be arranged in a square, a circle, or any other practical configuration.

Figure 8:
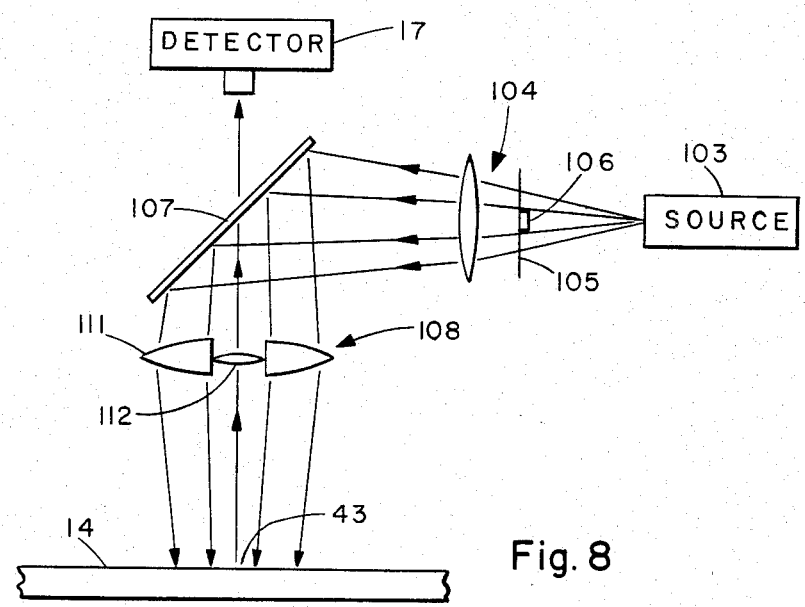
FIG. 8 is a diagrammatic view similar to FIG. 4 showing an altenative light source.

It is also possible to employ the apparatus shown in FIG. 8 for illumination of the circuit board surface. The light from source 103 passes through optics 104 which includes a mask 105. The mask is generally clear, but has an opaque area 106 which, by means of beam splitter 107 and lens system 108, provides dark area 43 on the surface of board 14. Lens system 108 is formed of a relatively large lens 111 with a center objective lens 112. With this system, as with those of FIGS. 2 and 6, a black or nonilluminated area is provided within which is positioned the detector field of view.

By means of the illumination apparatus disclosed herein, a circuit board inspection system can be devised which increases productivity and quality. Direct savings from such a system would be realized from elimination of inspector subjectivity, reduction of inspection cost, reliable process control information, reduction in scrap, rework and in warranty claims. This illumination system is not affected by conductive material or lamina thickness. A system using this illumination apparatus can be operated by unskilled operators, partly because the illumination system has no moving parts and yet it has a high sensitivity while being extremely stable. For some production requirements, there must be 100% circuit board inspection. This can take as much as several hours per board with existing machines, while apparatus using this illumination system can completely inspect the same boards in three minutes or less.

The apparatus is shown with the circuit board carriage moving in one direction and the illumination system moving in the orthogonal direction. It is quite possible to have one of the elements fixed and the other move in both directions with respect to it. The preferred embodiment has two top surface light sources 15, 16, but one such light source could be used. The oblique angle of the lights is shown to be about 45° but the angle is not critical. It is only important that light penetrate the substrate, be scattered and reflected, and provide detectable relative light and dark areas in the field of view, where circuitry is dark and absence of circuitry is light. As a routine matter, it is also necessary to avoid light reflected from top surface 26 from being sensed by detector 44.

This illumination system is effective with substrates ranging from 0.004 inch to in excess of 0.1875 inch in thickness, and provides 0.0003 inch resolution, more than adequate even for boards having extremely fine conductive paths or lines.

In light of the above description, it is likely that modifications and improvements will occur to those skilled in the art which are within the scope of the accompanying claims.

What is claimed is:

1. Apparatus for illuminating a circuit board for inspection thereof, said circuit board having a translucent substrate and conductive circuitry on at least one side thereof, said apparatus comprising:
   a frame;
   a first carriage mounted to said frame for holding said circuit boards during inspection thereof;
   a second carriage mounted to said frame and spaced from said first carriage, at least one of said carriages being movable on said frame and with respect to the other carriage;
   first light source means mounted to said second carriage and directed at an oblique angle to the surface to be inspected of said circuit board;
   first detector means sensitive to light from said first light source means, said first detector means being mounted to said second carriage in fixed relationship with respect to said first light source means and arranged to detect light in a predefined field of view on the surface of said circuit board; and
   means cooperatively arranged with said first light source means to limit illumination of that portion of said circuit board to a predefined area having an edge closely adjacent but spaced from said field of view;
   whereby light directed onto said surface by said first light source means penetrates said circuit board, is scattered and reflected therewithin, and illuminates said field of view, said first detector means determining the presence or absence of an opaque conductive element in said field of view by the level of light sensed, said conductive element being opaque with respect to said substrate at the wavelength of said first light source means.

2. The apparatus recited in claim 1 wherein said first detector means comprises a linear detector array of sensors defining a linear field of view.

3. The apparatus recited in claim 1 wherein said first detector means comprises a cross-shaped detector array of sensors defining a cross-shaped field of view.

4. The apparatus recited in claim 1 wherein said first light source means, first detector means and illumination limiting means comprise a circuit board inspection unit, said apparatus further comprising a plurality of circuit board inspection units, each illuminating a separate area of the circuit boards mounted on said first carriage.

5. The apparatus recited in claim 1 wherein said first light source means comprises two separate spaced light source, each being directed at an oblique angle toward but just short of said field of view.

6. The apparatus recited in claim 5 wherein said first light sources illuminate said predefined spaced areas of said surface to be inspected on opposite sides of said field of view, each said first light source having means to sharply define an edge of said predefined illuminated area, said edge being parallel and spaced from but closely adjacent said field of view.

7. The apparatus recited in claim 1 and further comprising means to move said first and second carriages with respect to each other so that said first detector means scans a path across said circuit board.

8. The apparatus recited in claim 7 and further comprising means to move said first and second carriages orthogonally with respect to each other so that said first detector means scans a predetermined portion of said surface to be inspected of said circuit board.

9. The apparatus recited in claim 1 wherein light directed onto said surface by said first light source means substantially surrounds said field of view.

10. The apparatus recited in claim 9 wherein said light source means comprises a filter shaped and configured to define a dark area within which said field of view is positioned.

11. The apparatus recited in claim 1 and further comprising:
    second light source means directed toward the side of said circuit board opposite to said surface to be inspected, said second light source means being further directed toward said first detector means.

12. The apparatus recited in claim 11 and further comprising:
    a third light source directing a narrow beam of light toward said opposite side of said circuit board and directly at said first detector means;
    second detector means for sensing light from said third light source passing through said circuit board; and
    comparator means coupled to said first and second detector means for determining the presence or absence of a hole through said circuit board.

13. The apparatus recited in claim 14 and further comprising filter means positioned between said third light source and said second detector means, said filter having a transmissive bandwidth sufficient to pass light from said third light source and exclude substantially all other light.

14. The apparatus recited in claim 12 wherein:
    said third light source comprises a laser; said apparatus further comprising:
    a first beam splitter positioned between said second light source and said opposite surface of said circuit board, said first beam splitter passing substantially all of the light from said second light source, said laser light being directed onto said first beam splitter and reflected thereby orthogonally toward said opposite side of said circuit board and said first detector means; and
    a second beam splitter positioned between said surface to be inspected and said first detector means, said second beam splitter directing said laser light away from said first detecting means, said second beam splitter passing substantially all of the light from said second light source.

15. The apparatus recited in claim 14 and further comprising filter means positioned between said laser and said second detector means, said filter having a transmissive bandwidth sufficient to pass said laser light and exclude substantially all other light.

16. A method of inspecting a circuit board having a translucent substrate and conductive circuitry on at least one surface thereof, said method comprising the steps of:
   directing at least one beam of light at an oblique angle onto the surface of said board to be inspected;
   viewing from above said surface by means of a first detector array a sharply defined field of view, said light beam having a defined edge on said surface closely adjacent but spaced from said field of view;
   illuminating said field of view on said surface from within said board by scattering and reflection of said light within said board; and
   detecting by means of sensors in said detector array light variations on said field of view from the scattered and reflected light within said circuit board indicative of the presence and absence in said field of view of conductive circuitry, said conductive circuitry being opaque with respect to said substrate at the wavelength of said light.

17. The method recited in claim 16 wherein said directing step comprises directing two separate spaced beams of light at oblique angles toward but just short of said field of view.

18. The method recited in claim 16 wherein said viewing step is accomplished by a linear array of sensors comprising said detector array, resulting in a linear field of view.

19. The method recited in claim 16 wherein said viewing step is accomplished by a cross-shaped array of sensors comprising said detector array, resulting in a cross-shaped field of view.

20. The method recited in claim 16 wherein said light beam substantially surrounds said field of view and defines a dark area within which said field of view is positioned.

21. The method recited in claim 16 and further comprising the step of directing a third beam of light toward the opposite side of said circuit board and directly toward said detector array.

22. The method recited in claim 21 and further comprising the steps of:
   directing a sharply defined narrow fourth beam of light onto said opposite side of said circuit board in alignment with said detector array;
   detecting any portion of said fourth beam of light passing through said circuit board by means of a second detector; and
   comparing the outputs of said first detector array and said second detector to ascertain presence or absence of a hole through said circuit board.

23. The method recited in claim 16 and comprising the further step of moving said circuit board with respect to said light beam and detector array to scan a path across said circuit board by said detector array.

24. The method recited in claim 23 wherein said moving step comprises orthogonal relative motion so that said detector array scans a predetermined portion of said surface to be inspected of said circuit board.

25. A method of inspecting a circuit board having a translucent substrate and conductive circuitry on at least one surface thereof, said method comprising the steps of:
   directing light at an oblique angle onto a predetermined portion of the surface of said board to be inspected;
   blanking an area of said light on said surface to leave said area dark;
   viewing from above said surface by means of a first detector array a sharply defined field of view within said dark area, said light having a defined edge on said surface closely adjacent but spaced from said field of view;
   illuminating said field of view on said surface from within said board by scattering and reflection of said light within said board; and
   detecting by means of sensors in said detector array light variations on said field of view form the scattered and reflected light within said circuit board indicative of the presence and absence in said field of view of conductive circuitry, said conductive circuitry being opaque with respect to said substrate at the wavelength of said light.

* * * * *

UNITED STATES PATENT AND TRADEMARK OFFICE
CERTIFICATE OF CORRECTION

PATENT NO. : 4,538,909

DATED : September 3, 1985

INVENTOR(S) : ROBERT E. BIBLE, ROBERT E. BIBLE JR. and RICHARD S. MASON

It is certified that error appears in the above-identified patent and that said Letters Patent are hereby corrected as shown below:

Column 7, line 67, Claim 5, change "source" to --sources--.

Signed and Sealed this

Eighteenth Day of February 1986

[SEAL]

Attest:

DONALD J. QUIGG

Attesting Officer

Commissioner of Patents and Trademarks